(12) United States Patent
Bosaeus et al.

(10) Patent No.: US 9,194,833 B2
(45) Date of Patent: Nov. 24, 2015

(54) ABSORBENT ARTICLE COMPRISING A LIQUID DISCHARGE SENSOR

(75) Inventors: Mattias Bosaeus, Kållered (SE); Allan Elfström, Philadelphia, PA (US); Fredrik Mellbin, Kållered (SE)

(73) Assignee: SCA HYGIENE PRODUCTS AB, Göteborg (SE)

( * ) Notice: Subject to any disclaimer, the term of this patent is extended or adjusted under 35 U.S.C. 154(b) by 263 days.

(21) Appl. No.: 13/996,944

(22) PCT Filed: Dec. 20, 2011

(86) PCT No.: PCT/EP2011/073454
§ 371 (c)(1),
(2), (4) Date: Aug. 1, 2013

(87) PCT Pub. No.: WO2012/084985
PCT Pub. Date: Jun. 28, 2012

(65) Prior Publication Data
US 2013/0307570 A1 Nov. 21, 2013

(30) Foreign Application Priority Data
Dec. 23, 2010 (GB) .................................. 1022029.1

(51) Int. Cl.
*G01N 27/04* (2006.01)
*G01N 27/07* (2006.01)
(Continued)

(52) U.S. Cl.
CPC .............. *G01N 27/048* (2013.01); *A61F 13/42* (2013.01); *G01N 27/07* (2013.01); *A61B 5/6808* (2013.01)

(58) Field of Classification Search
CPC .... G01N 27/07; G01N 27/048; A61F 13/428; A61F 13/42
See application file for complete search history.

(56) References Cited

U.S. PATENT DOCUMENTS

| 4,356,818 A | 11/1982 | Macias et al. |
| 5,838,240 A | 11/1998 | Johnson |

(Continued)

FOREIGN PATENT DOCUMENTS

| AU | 63393/94 A | 12/1994 |
| GB | 2219679 A | 12/1989 |

(Continued)

OTHER PUBLICATIONS

Chinese Office Action dated Jun. 3, 2014 (and English translation thereof) issued in corresponding Chinese patent application No. 201180061131.5 (11 pages).

*Primary Examiner* — Van Trieu
(74) *Attorney, Agent, or Firm* — Drinker Biddle & Reath LLP

(57) ABSTRACT

An absorbent article for absorbing liquid discharge of a wearer includes conductive loops each in an open loop shape having terminal ends for electrically communicating with opposing poles of an electric potential generator such that current flows around the full conductive loop between the terminal ends when a space defined within the open loop shape is dry and such that liquid discharge in the space defined within the open loop shape is able to cause a short circuit in the conductive loop so that the current flows around a reduced impedance path. The impedance change is measurable to determine a location relative to the terminal ends where the liquid discharge has caused the short circuit. The conductive loops are oriented such that the direction in which the current travels up an outward leg of the respective conductive loop is in substantially the opposite direction for a first conductive loop as for a second conductive loop.

19 Claims, 1 Drawing Sheet

(51) Int. Cl.
*A61F 13/42* (2006.01)
*A61B 5/00* (2006.01)

(56) References Cited

U.S. PATENT DOCUMENTS

| 6,774,800 | B2 * | 8/2004 | Friedman et al. | 340/573.5 |
| 7,394,391 | B2 * | 7/2008 | Long | 340/573.5 |
| 7,642,396 | B2 * | 1/2010 | Ales et al. | 340/573.5 |
| 7,956,754 | B2 * | 6/2011 | Long | 340/573.5 |
| 2005/0046578 | A1 | 3/2005 | Pires | |
| 2006/0244614 | A1 * | 11/2006 | Long | 340/573.5 |
| 2007/0024457 | A1 * | 2/2007 | Long et al. | 340/605 |
| 2007/0252713 | A1 * | 11/2007 | Rondoni et al. | 340/573.5 |
| 2007/0270774 | A1 | 11/2007 | Bergman et al. | |
| 2009/0315728 | A1 | 12/2009 | Ales, III et al. | |

FOREIGN PATENT DOCUMENTS

| JP | 2-174846 A | 7/1990 |
| JP | 2002-082080 A | 3/2002 |
| JP | 2010-172426 A | 8/2010 |
| WO | WO-2008/024860 A2 | 2/2008 |

\* cited by examiner

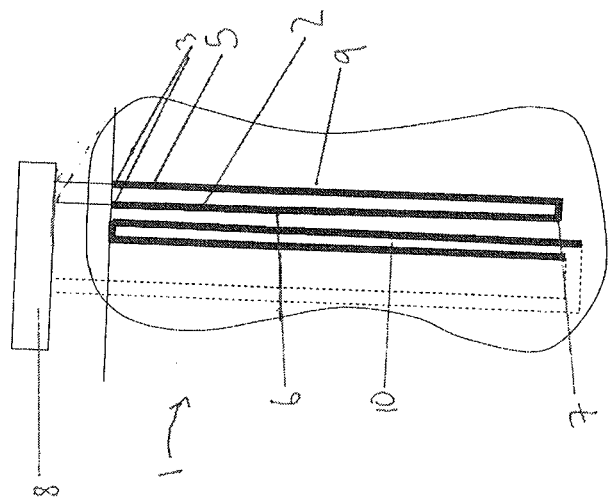
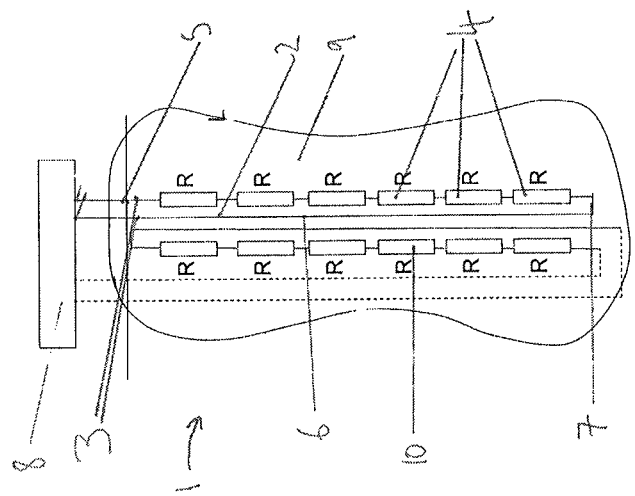
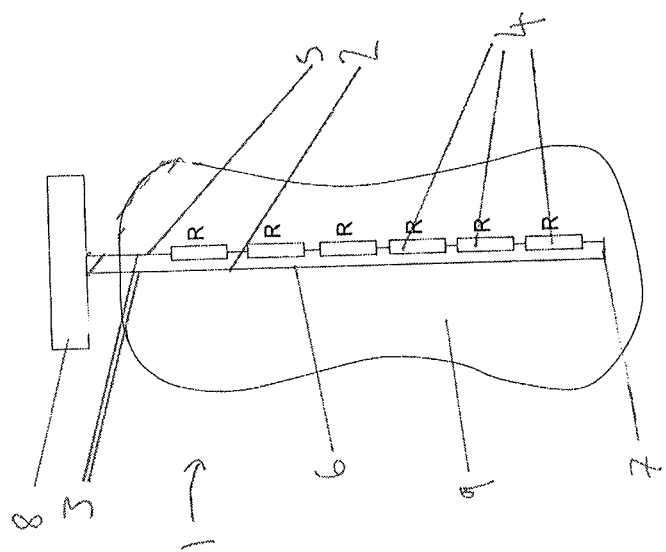

ABSORBENT ARTICLE COMPRISING A LIQUID DISCHARGE SENSOR

CROSS-REFERENCE TO PRIOR APPLICATION

This application is a §371 National Stage Application of PCT International Application No. PCT/EP2011/073454 filed Dec. 20, 2011, which claims priority to GB 1022029.1, filed Dec. 23, 2010, both of which are incorporated herein in their entirety.

TECHNICAL FIELD

The present disclosure relates to an absorbent article that includes a liquid discharge sensor.

BACKGROUND

Absorbent articles including a liquid discharge sensor are known in the art. One example prior art arrangement is provided in Australian patent publication AU-B-63393/94. The sensor of this prior art document is provided in the form of a pair of spaced electrically conductive strips mounted on a length of insulating material. The strips are suitably positioned within the absorbent article to be conductively bridged and thereby short-circuited by a wetting of an absorbent pad into which the band has been inserted. Conductivity between the first and second strips is substantially zero when the absorbent pad is dry, but increases sharply when moistened by a liquid discharge event. The sensor is thus disclosed to act as a switch to indicate when a liquid discharge event has occurred.

It may be of interest to learn the extent of spread in the absorbent pad of the liquid discharge, for example so as to analyse the absorbency performance of the absorbent article. It may be further desirable to provide a means for verifying that the liquid discharge sensor is functioning properly, i.e. that there are no breaks along the conductive strip.

SUMMARY

The present disclosure provides an absorbent article for absorbing liquid discharge of a wearer when worn in the crotch region, the liquid discharge being, for example, urination, menstruation or liquid faecal matter. The absorbent article includes a conductive open loop having terminal ends for electrical communication with opposing poles of an electric potential generator such that liquid discharge in the space defined within the open loop is able to cause a short circuit in the open loop and so that the current flows around a reduced impedance path as compared to the impedance of the full open loop, wherein the impedance change is measureable to determine a location relative to the terminal ends where the liquid discharge has caused the short circuit.

The present disclosure thus provides a way of determining the position of a liquid discharge. A potential is applied between the terminal ends such that the extent of the impedance loop that the current travels around depends on whether or not there has been a liquid discharge within the loop and, if so, how close to the terminal ends the discharge has spread to. A full loop current flow path presents the highest impedance and indicates that there is not yet sufficient liquid discharge within the loop to cause a short circuit. A partial loop current flow path indicates that a liquid discharge has caused a short circuit so that current does not flow around the full loop. Depending on the impedance suffered by the current flow, the extent of the impedance loop within which the current has travelled can be determined, thereby indicating how close to the terminal ends the liquid discharge has spread. As the liquid discharge is bodily fluids, the loop has to be made of a sufficiently high impedance material for the bodily fluids to offer a path of least resistance for the short circuit to occur. That is, the conductive loop is of higher resistance to current flow than the absorbent article when wet in the space defined by the loop.

In particular embodiments, the first conductive loop is in electrical contact with an element of the absorbent article and the terminal ends are at a contact point where the electrical contact is made between the conductive loop and said element. Thus, the terminal ends could be a division between insulated portions of a conductor relative to said element and a portion electrically exposed to said element. The element could be a leg elastic portion or opposing leg elastic portions or a particular layer of the absorbent article or the absorbent core of said absorbent article. In a certain embodiment, the short circuit is such that electric current flows through the element of the absorbent article that has been wetted by the liquid discharge between a first point on the conductive loop and a second point on the conductive loop. The first and second points on the conductive loop are points where the electric current has diverted through the wetted absorbent article element and the second point is where the electric current re-joins the conductive loop as caused by the spread of the liquid discharge over the conductive loop.

In particular embodiments, the open loop is located so as to short circuit under liquid discharge within an absorbent core of the absorbent article, thereby allowing information to be gathered on liquid discharge presence and its spread within the absorbent core.

In an alternative embodiment, the open loop is located so as to short circuit under liquid discharge peripherally, i.e. laterally outside, of an absorbent core of the absorbent article, such as within standing gathers or at least one leg elastic portion of an absorbent article, such as diaper or adult incontinence article, thereby allowing liquid discharge leakage to be detected. Although the present disclosure is primarily concerned with baby or toddler diaper or adult incontinence absorbent articles, it is believed to be generally applicable to other absorbent articles such as sanitary towels.

In a certain embodiment, the resistance of the open conductive loop per centimeter of the conductive loop is at least of the order of 1 Ohm/cm (i.e. 1-9 Ohms/cm), of the order of 10 Ohms/cm (i.e. 10, 20 . . . 80, 90 Ohms/cm), of the order of 100 Ohms/cm or of the order of 1000 Ohms/cm.

To determine the resistance per centimeter in the conductive loop, one can position a conductive bridge of an extremely high conductivity wire (such as copper or silver) across opposing portions of the conductive loop at a position 25% in distance from the terminal ends of the resistive conductive loop to the distal end of the resistive conductive loop, 50% of the distance, at 75% of the distance and at the full extent of the conductive loop. The straight line distance from the terminal ends to the 25% bridge, to the 50% bridge, to the 75% bridge and to the distal end of the conductive loop from a position at the opposing terminal ends of the resistive conductive loop can then be taken in centimeters. The terminal ends of the conductive loop are to be taken as the point of first electrical contact of the conductive loop with the absorbent core or other absorbent article element. The measured resistance when a potential is applied between the terminal ends for the 25% bridge, the 50% bridge, the 75% bridge and the full conductive loop can then be taken. The resistance values divided by the distance values in centimeters will then give a respective reading for the resistance per unit length in centimeters of the conductive loop from which an average of the four values can be taken to determine the resistance per centimeter of the conductive loop.

In this way, the conductive loop offers far greater resistance to the passage of electric current than the liquid discharge in the absorbent article, which means that the point of first short circuit relative to the terminal ends will provide a path of least resistance for practically all of the current applied to the conductive loop so that the current flows only around a portion of the conductive loop and only an insignificant amount of current will flow around the full conductive loop. Thus, a measurement of resistance or impedance to current travelling in the loop will indicate accurately that a partial loop has been traversed and will also indicate the extent of the partial loop to determine where the short circuit, and thus the liquid discharge, has occurred relative to the terminal ends.

The high resistance can be implemented in the conductive loop by way of discreet resistive elements positioned at spaced apart locations or by way of the conductive loop itself being made of a resistive material.

In particular embodiments, the conductive loop includes an outward leg, a return leg and a connecting portion therebetween. The outward leg and the return leg can be evenly spaced apart from one another. The legs may be linear and thus parallel to one another.

In a further certain embodiment, the conductive loop is elongate (that is longer along a long axis than a short axis) and is positioned in the absorbent article so as to be generally aligned with a longitudinal axis of the absorbent article (that is the long axis of the conductive loop is generally aligned with the longitudinal axis of the absorbent article).

This is particularly advantageous when the conductive loop is positioned so as to detect liquid discharge in the absorbent core since it allows one to determine the longitudinal spread of liquid discharge within the absorbent core relative to the terminal ends, which is a useful indicator of the overall extent of the liquid discharge if an assumption of the liquid source point is taken and assuming a substantially longitudinally symmetrical spread of discharge.

In a certain embodiment, the conductive loop extends over at least 30% of a full longitudinal extent of an absorbent core of the absorbent article, 40%, 50%, 60%, 70%, 80% or perhaps even 90%.

Such a longitudinal coverage of the absorbent article will ensure that a liquid discharge event is detected and its spread can be determined even for liquid discharge events extending to less common longitudinal positions in the absorbent core.

In a yet further certain embodiment, the conductive loop includes an outward leg, a return leg and a connecting portion between the legs and the absorbent article includes a second such conductive loop, wherein the connected portions of the first and second conductive loops are disposed in opposition to one another.

Thus, the general direction from the terminal ends to the connecting portion of the first conductive loop goes in one direction, while the same line for the second conductive loop goes in the opposite direction with respect to the absorbent article. This offers an the feature that the liquid discharge extent in opposing directions can be determined, thereby allowing a good estimation of the overall extent of the spread of the liquid discharge assuming a generally planar, or more particularly circular liquid discharge footprint.

The second conductive loop can have any and all of the features for the first conductive loop discussed above.

Put another way, the absorbent article includes a second conductive open loop having terminal ends for electrically communicating with opposing poles of an electrical potential generator. The first and second conductive loops are elongate and arranged relative to one another such that a planar, or more particularly circular footprint liquid discharge centered in a gap between the first and second conductive loops and which is contained within the first and second conductive loops with respect to a long axis of the first and second conductive loops causes a short circuit in the first and second conductive loops. This short circuit will occur at a location relative to the terminal ends of the first conductive loop that is on an opposite side of the circular liquid discharge to the short circuit location relative to the terminal end of the second conductive loop, or more particularly at diametrically opposite sides of the circular liquid discharge.

Put yet another way, the absorbent article can include a second conductive open loop, wherein the first and second conductive loops include an outward leg, a return leg and a connecting portion therebetween. Assuming current flows in one direction up the outward leg in electrical contact with the absorbent article, or in particular the absorbent core, said one direction for the first conductive loop is opposite to said one direction for the second conductive loop.

Alternatively put, the absorbent article includes a second conductive open loop that has terminal ends for being in electrical communication with opposing poles of an electrical potential generator, wherein the first and second conductive loops are elongate and a line extending along a long axis of a first conductive loop from the terminal ends extends in an opposite sense to a line extending along the long axis of the second conductive loop from the terminal ends.

In particular embodiments, the first and second conductive loops are the same shape and size as one another when viewed in plan relative to a laid out flat absorbent article.

In particular embodiments, the first and second loops are arranged so as to short circuit under a liquid discharge absorbed by the absorbent core. Thus, the loops could be embedded in the absorbent core, could be placed underneath the absorbent core, yet in physical and electrical contact therewith, or otherwise placed in electrical contact with the absorbent core.

In particular embodiments, the first and second conductive loops are arranged closely adjacent to one another so that a liquid discharge of about 25 ml centered in a gap between the first and second conductive loops will cause a short circuit in both conductive loops. For absorbent articles where the detection of larger quantities of liquid discharge is acceptable, the 25 ml short circuit criteria could be increased, for example, to about 50 ml or about 100 ml.

In the case where the first and second loops both include linear outward and return leg portions, these linear portions can be parallel to one another.

As described above, the first and second conductive loops can be arranged longitudinally with respect to the absorbent article, where the long axis of the first and second conductive loops is generally aligned with a longitudinal axis of the absorbent core, yet the first and second conductive loops are laterally spaced from one another.

The use of just two conductive loops is considered sufficient to accurately enough determine the extent and location of liquid discharge. Nonetheless, if finer resolution is needed, greater numbers of loops could be used and still be within the scope of the claims.

In a second aspect, there is provided a system including an absorbent article for absorbing liquid discharge of a wearer when worn in the crotch region of the wearer, wherein the absorbent article includes a conductive open loop having terminal ends, the system including an electrical property measurement unit that is configured to apply an electric potential between the terminal ends such that electric current flows around the full open loop unless there is a short circuit caused by a liquid discharge in the space defined inside the conductive open loop, the short circuit causing electric current to flow around a reduced impedance path as compared to the impedance of the full open loop, and a liquid discharge location determination unit that is configured to determine a location of the short circuit relative to the terminal ends based on predetermined data concerning the electrical property of the conductive path and an electrical property measured by the electrical property measurement unit when applying the potential between the terminal ends of the conductive open loop.

In particular embodiments, the predetermined data relates the electrical property to short circuit position, wherein the electrical property changes depending on whether there is or is not a short circuit and changes depending on the position relative to the terminal ends of the short circuit. In particular embodiments, the electrical property is impedance.

The initial value of the electrical property before any liquid discharge in the loop is useful for system check purposes. Assuming the electrical property breaches a predetermined threshold, it can be taken that the loop is sufficiently conductive for determining liquid discharge data (i.e. there are no conductive breaks in the loop). Further, the initial or article dry value for the electrical property can be used to calibrate the algorithm for determining the location of the liquid discharge. The initial value provides a reference point from which the change in electrical property after liquid discharge can be obtained to determine the location of the liquid discharge relative to the terminal ends of the conductive loop.

The terminal ends of the conductive loop are to be understood as the start of the conductive loop in electrical contact (uninsulated) with the absorbent article, or in particular, the absorbent core.

In particular embodiments, the second aspect is combined with the first aspect described above. Thus, the conductive loop has the features described above for the conductive loop.

Further, the system can further include a second conductive loop having terminal ends and the electrical property measurement circuit is configured to also apply a potential between the terminal ends in order to determine the electrical property related to current flow around the second conductive open loop, wherein the liquid discharge location determination unit is configured to also determine the location of the liquid discharge relative to the terminal ends of the second conductive loop based on the measured electrical property in the second conductive open loop and predetermined data concerning the electrical property of the second conductive loop.

In particular embodiments, the second conductive loop includes the features described above for the second conductive loop.

The liquid discharge location determination unit is able to determine the location of the short circuit relative to the terminal ends since it has predetermined information on the electrical property, e.g. impedance, in the conductive loops that would be obtained by short circuits at any given distance from the terminal ends. Thus, by comparing the measured impedance in the loops with the known impedance values for a given distance, the liquid discharge location unit is able to determine the information concerning the location of the short circuit and thus the spread of the liquid discharge with respect to the first and second conductive loops.

In a certain form, the first and second conductive loops are arranged in reverse relative to one another so that the positions of the short circuits in the first and second conductive loops is caused by opposed ends of a liquid discharge. Put another way, the first and second conductive loops are oriented such that the direction in which the current travels up an outward leg of the conductive loop, and ultimately flows through the resistive means in the conductive loop, is in substantially the opposite direction for the first conductive loop as for the second conductive loop.

In a certain embodiment, impedance measurements are taken repeatedly and the system includes a recording unit that is configured to record data produced by the system so that the spread of the liquid discharge over time can be measured and recorded. This feature provides useful information concerning absorbency properties of the absorbent article.

In particular embodiments, the measurement unit is configured to apply a potential between the terminal ends of the first conductive loop and the second conductive loop sequentially. Thus, there can be an interval between performing measurement operation on each conductive loop so as to avoid interference between the two loops, thereby affecting the electrical property measurement results.

In particular embodiments, the system further includes a volume estimation unit that is configured to calculate an estimated volume of the liquid discharge based on the location of opposed ends of the liquid discharge as determined by the location of the short circuit in the first conductive loop and the location of the short circuit in the second conductive loop. An indication of volume of liquid discharge is useful in assessing the absorbency performance of the absorbent article as well as whether a particular wearer or patient is adorning the appropriate absorbency level absorbent garment.

BRIEF DESCRIPTION OF THE FIGURES

FIG. 1 discloses an absorbent core for an absorbent article that includes a plurality of discreet resistors on one leg of the loop for measuring liquid discharge spread in the conductive loop.

FIG. 2 discloses a second embodiment of an absorbent core that includes first and second conductive loops that are of the form of the conductive loop shown in FIG. 1 but where the conductive loops face in opposite directions to one another so that the spread of a liquid discharge can be measured from reference points disposed on either side of the liquid discharge to thereby give an indication of the area of the liquid discharge.

FIG. 3 discloses an absorbent core for an absorbent article having first and second conductive loops arranged in the same sense with respect to one another as that shown in FIG. 2 but the resistors have been replaced by continuously resistive conductive material, such as resistive conductive ink.

DETAILED DESCRIPTION OF PREFERRED EMBODIMENTS

In FIG. 1, there is disclosed an absorbent core 1 for an absorbent article. The absorbent core 1 is integrated into an absorbent article by disposing it and capturing it between a top sheet of the absorbent article, for allowing liquid discharge to enter the absorbent article, and a backsheet that is liquid impermeable to prevent escape of the liquid discharge from the absorbent article. The absorbent core 1 is designed to absorb liquid discharge such as urination, menstruation or liquid faecal matter when worn in the crotch region.

In the embodiment of FIG. 1, there is shown a conductive loop 2 having terminal ends 3 such that the conductive loop 2 is open at the terminal ends 3. The conductive loop 2 is in electrical contact with the absorbent core 1 so that the absorbent core being wet affects the conduction of electric current about the conductive loop 2. The terminal ends 3 are the points where the conductive loop 2 is brought into electrical contact with the absorbent core 1. They are the start and finish of the conductive loop 2 in relation to current travelling around the conductive loop 2 in electrical contact with the absorbent core 1.

The conductive loop includes a plurality of resistors 4 (in the shown configuration there are six resistors, but any suitable number of resistors can be used) that are arranged along an outward leg 5 of the conductive loop 2 and spaced from one another therealong. The conductive loop 2 further includes a return leg 6 and a connection portion 7 therebetween. The outward leg 5 and the return leg 6 are linear and are spaced apart laterally from one another with respect to a longitudinal axis of the absorbent core 1 so as to define parallel outward and return legs 5, 6 of the conductive loop 2. In the embodiment of FIG. 1, the conductive loop 2 is made of a conductive wire that connects the resistors 4. The conductive wires are secured to the backsheet of the absorbent article. The conductive wires could be threads coated in a conductive metal, conductive graphite or conductive polymer. The conductive loop 2 is, in another certain form, printed on a backsheet of the absorbent article yet in electrical contact with the absorbent core 1.

A control unit 8 is in electrical communication with the terminal ends 3 of the conductive loop 5. The control unit 8 is configured to apply a potential between the outward and return legs 5, 6 and to measure the impedance between them. The control unit 8 is further configured to perform the impedance measurement periodically and to record the data obtained in association with the time that the measurement was made.

When the absorbent core 1 is in a dry state, the control unit will measure a maximum impedance for conductive loop 2. Thus, assuming a resistance of 20 kOhms for each of the six resistors 4, the control unit 8 would measure an impedance or resistance of 120 kOhms. When a liquid discharge 9 is subjected to the conductive loop 2, there will occur a short circuit between the outward leg 5 and the return leg 6 of the conductive loop 2 such that the current applied by the control unit 8 goes around only a partial extent of the conductive loop 2 and encompasses some but not all of the resistors 4. Accordingly, the liquid discharge 9 will cause the control unit 8 to measure a reduced impedance corresponding to the number of resistors 4 that the short circuited partial conductive loop 2 encompasses. Thus, with a liquid discharge 9 as shown in FIG. 1, there is a short circuit between the second and third resistors (as measured from the control unit 8), which will cause the conductive path to be shortened so as to encompass only the first two resistors 4. Accordingly, the control unit will measure an impedance of 40 kOhms when the resistors have a resistance of 20 kilo Ohms each.

The control unit 8 is thus configured to take the impedance measurement and determine an extent of the liquid discharge 9 (or more specifically the short circuit) as a distance measured from the terminal ends 3 of the conductive loop 2. It is thus possible to make a determination that the liquid discharge 9 has reached a location between the second and third resistors. Alternatively, the control unit 8 could conceptually split the absorbent core 1 into 6 zones, where each zone includes a corresponding resistor 4 and determine that the liquid discharge has not yet reached given zones based on the impedance measurement.

The control unit may be further configured to estimate a volume of the liquid discharge 9 based on an assumption of where the origin of the liquid discharge 9 is likely to have been and assuming longitudinal symmetry of the liquid discharge about the origin. This assumption will allow an estimated extent of the discharge to be made, which can be approximately correlated with a liquid discharge volume.

The control unit 8 is configured to record the impedance measurements over time for subsequent data analysis purposes.

The control loop 2 offers verification that the liquid discharge detector is functioning properly because any break in the conductive loop 2 would prevent the control unit 8 from passing a current around the conductive loop 2 when the absorbent core 1 is dry, thereby indicating that something is wrong with the conductive circuit.

In the second embodiment shown in FIG. 2, the absorbent core 1 has a second conductive loop 10 that is essentially the same as the first conductive loop 2 (it has the same number of resistors, it is of the same shape and size and is made of the same materials) yet is arranged in the opposite direction to the first conductive loop 2 so that current applied to the terminal ends by the control unit 8 passes through the resistive means 4 from opposite ends of the absorbent core with respect to the longitudinal axis of the absorbent core. Thus, for the first conductive loop 2, the first resistor 4 is located at one end of the absorbent core 1 and for the second conductive loop 10, the first resistor 4 is located at the opposite end of the absorbent core 1. In this way, the length of the conductive loop 2, 10 through which current applied by the control unit 8 passes is measured from opposite ends of the absorbent core 1. Put another way, the connecting portion 7 of the first conductive loop 2 is disposed at an opposite end of the absorbent core 1 to the connecting portion 7 of the second conductive loop 10.

In the dry state, the control unit 8 will measure an impedance corresponding to the full impedance of the sum of the resistors 4 in each of the first and second conductive loops 2, 10. This data is further useful in verifying that the conductive loops 2, 10 are operational.

When a liquid discharge 9 is spread over the first and second conductive loops 2, 10, the current will flow to the short circuit in the first conductive loop 2 in one direction and will flow to the short circuit in the second conductive loop 10 in an opposite direction to the first direction. This thus allows the liquid discharge 9 to be measured from opposite points of view, thereby allowing an indication of opposing extents of the liquid discharge 9.

According to the specific liquid discharge 9 shown in FIG. 2, a short circuit is present between the first and second resistors 4 in the first conductive loop 2 and a short circuit is present between the third and fourth resistors 4 in the second conductive loop 10. Assuming each of the resistors in each of the loops has a resistance of 20 kOhms, the control unit will measure an impedance of 20 kOhms in the first conductive loop 2 and 60 kOhms in the second conductive loops 10. Using predetermined information concerning the location of the resistors 4 in each of the conductive loop 2, 10, the control unit 8 can output a graphical or other illustration of the location and longitudinal extent of the liquid discharge 9. Further, the control unit 8 can take an assumption on the shape of the liquid discharge 9 and, using predetermined data concerning the volume of a liquid discharge for a given longitudinal extent of the liquid discharge 9, a volume estimation can be made for the liquid discharge 9.

In the embodiment of FIG. 3, there is disclosed an absorbent core 1 similar to those shown in FIGS. 1 and 2 and having first and second conductive loops 2, 10 that are arranged in the same sense as the conductive loops 2, 10 shown in FIG. 2. In the embodiment of FIG. 3, the conductive loops are made of highly resistive conductive material such as highly resistive ink printed on the backsheet of the absorbent article and in electrical contact with the absorbent core 1. Alternatively, the loops can be made of highly resistive threads secured to the backsheet and in electrical contact with the absorbent core 1. The resistive material could have a resistance of the order of 1 kOhm per linear centimeter of conductive material. In the embodiment of FIG. 2, the accuracy of liquid discharge location detection is limited to the resolution provided by the discreet resistors 4. Thus, the less resistors 4 there are, the lower the accuracy with regard to determining the spread of the liquid discharge 9. In the embodiment of FIG. 3, the resistance changes continuously, rather than in discreet portions as in the embodiment of FIG. 2, thereby allowing optimally fine resolution in determining the longitudinal extent of the liquid discharge 9.

The invention claimed is:

1. An absorbent article for absorbing liquid discharge of a wearer when worn in the crotch region, the liquid discharge being urination, menstruation or liquid faecal matter, the absorbent article comprising at least one conductive loop in an open loop shape having terminal ends for electrically communicating with opposing poles of an electric potential generator such that current flows around the full conductive loop between the terminal ends when a space defined within the open loop shape is dry and such that liquid discharge in the space defined within the open loop shape is able to cause a short circuit in the conductive loop so that the current flows around a reduced impedance path as compared to the impedance of the full conductive loop, wherein the impedance change is measurable to determine a location relative to the terminal ends where the liquid discharge has caused the short circuit, wherein the at least one conductive loop is a first conductive loop, the article comprises a second such conductive loop, and wherein the first and second conductive loops are oriented such that the direction in which the current travels up an outward leg of the respective conductive loop is in substantially the opposite direction for the first conductive loop as for the second conductive loop.

2. The absorbent article of claim 1, wherein the conductive loops is located so as to short circuit under liquid discharge within an absorbent core of the absorbent article.

3. The absorbent article of claim 2, wherein the terminal ends respectively provide a start and finish point of the conductive loop with respect to the conductive loop being in electrical contact with the absorbent core.

4. The absorbent article of claim 1, wherein resistance of the conductive loops per centimeter of the conductive loop is at least of the order of 1 Ohms/cm.

5. The absorbent article of claim 1, wherein the conductive loops comprise or consist of an outward leg, a return leg and a connecting portion therebetween.

6. The absorbent article of claim 5, wherein the outward leg and the return leg are evenly spaced apart from one another.

7. The absorbent article of claim 5, wherein the legs are linear and parallel to one another.

8. The absorbent article of claim 1, wherein the conductive loops are elongate and is positioned in the absorbent article so as to be generally aligned with a longitudinal axis of the absorbent article.

9. The absorbent article of claim 1, wherein each conductive loop extends over at least 30% of a full longitudinal and/or lateral extent of an absorbent core of the absorbent article.

10. The absorbent article of claim 1, wherein the conductive loops are embedded in the absorbent core in electrical communication therewith, are placed underneath the absorbent core yet in physical and electrical contact therewith or otherwise placed in electrical contact with the absorbent core.

11. The absorbent article of claim 1, wherein the first and second conductive loops are the same shape and size as one another when viewed in plan relative to a laid out flat absorbent article.

12. The absorbent article of claim 1, wherein the first and second conductive loops are arranged so as to respectively short circuit under a liquid discharge absorbed by the absorbent core.

13. The absorbent article of claim 1, wherein the first and second conductive loops are arranged closely adjacent to one another so that a liquid discharge of about 25 ml centered in a gap between the first and second conductive loops will cause a short circuit in both conductive loops.

14. The absorbent article of claim 1, further comprising an electrical property measurement unit configured to:
 apply a potential between the terminal ends;
 measure impedance of the first conductive loop and the second conductive loop; and
 determine an extent of liquid discharge in the article based on which of the first plurality of resistors and the second plurality of resistors have been short circuited.

15. The absorbent article of claim 1, wherein the first plurality of resistors is disposed linearly on an outward leg of the first conductive loop and spaced evenly therealong.

16. A system comprising an absorbent article for absorbing liquid discharge of a wearer when worn in the crotch region of the wearer, wherein the absorbent article comprises at least one conductive loop in an open loop shape having terminal ends, the system comprising an electrical property measurement unit that is configured to apply an electric potential between the terminal ends such that electric current flows around the full conductive loop unless there is a short circuit caused by a liquid discharge in the space defined inside the conductive open loop, the short circuit being so that electric current flows around a reduced impedance path as compared to the impedance of the full loop, and an electrical liquid discharge location unit that is configured to determine a location of the short circuit relative to the terminal ends based on an electrical property measured by the electrical property measurement unit when applying the potential between the terminals of the conductive loop, and predetermined data concerning the electrical property of the conductive path, wherein the at least one conductive loop is a first conductive open loop and the absorbent article comprises a second conductive open loop having terminal ends and the electrical property measurement circuit is configured to also apply a potential between the terminal ends in order to determine the impedance to current flow around the second conductive loop, wherein the liquid discharge location determination unit is configured to determine the location of the liquid discharge relative to the terminal ends of the second conductive loop based on the measured electrical property in the second conductive loop and predetermined data concerning the electrical property of the second conductive loop, wherein the first and second conductive loops are reverse arranged relative to one another so that the position of the short circuits in the first and second conductive loops is caused by opposed ends of a liquid discharge.

17. The system of claim 16, wherein impedance measurements are taken repeatedly and continuously, and the system comprises a recording unit that is configured to record data produced by the electrical property measurement unit and/or the liquid discharge location unit so that the spread of the liquid discharge over time can be measured and recorded.

18. The system of claim 16, wherein the electrical property is impedance.

19. An absorbent article for absorbing liquid discharge of a wearer when worn in the crotch region, the liquid discharge being urination, menstruation or liquid faecal matter, the absorbent article comprising at least one conductive loop in an open loop shape having a first plurality of resistors and terminal ends for electrically communicating with opposing poles of an electric potential generator such that current flows around the full conductive loop between the terminal ends when a space defined within the open loop shape is dry and such that liquid discharge in the space defined within the open loop shape is able to cause a short circuit in the conductive loop so that the current flows around a reduced impedance path as compared to the impedance of the full conductive loop, wherein the impedance change is measurable to determine a location relative to the terminal ends where the liquid discharge has caused the short circuit, wherein the at least one conductive loop is a first conductive loop, the article comprises a second such conductive loop that comprises a second plurality of resistors, and wherein the first and second conductive loops are oriented such that the direction in which the current travels up an outward leg of the respective conductive loop is in substantially the opposite direction for the first conductive loop as for the second conductive loop.

\* \* \* \* \*